(12) United States Patent
Muthukumar (10) Patent No.: US 10,736,863 B2
(45) Date of Patent: *Aug. 11, 2020

(54) METHODS OF INHIBITING CATARACTS AND PRESBYOPIA

(71) Applicant: UNIVERSITY OF MASSACHUSETTS, Boston, MA (US)

(72) Inventor: Murugappan Muthukumar, Amherst, MA (US)

(73) Assignee: UNIVERSITY OF MASSACHUSETTS, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/349,334

(22) Filed: Nov. 11, 2016

(65) Prior Publication Data

US 2017/0135972 A1 May 18, 2017

Related U.S. Application Data

(60) Provisional application No. 62/254,863, filed on Nov. 13, 2015.

(51) Int. Cl.

| *A61K 31/197* | (2006.01) |
|---|---|
| *A61K 31/4015* | (2006.01) |
| *A61K 9/00* | (2006.01) |
| *A61K 31/195* | (2006.01) |
| *A61K 31/765* | (2006.01) |
| *G02C 7/04* | (2006.01) |

(52) U.S. Cl.
CPC .......... *A61K 31/197* (2013.01); *A61K 9/0048* (2013.01); *A61K 31/195* (2013.01); *A61K 31/4015* (2013.01); *A61K 31/765* (2013.01); *G02C 7/04* (2013.01)

(58) Field of Classification Search
None
See application file for complete search history.

(56) References Cited

U.S. PATENT DOCUMENTS

| 4,351,826 A | 9/1982 | Clark et al. |
|---|---|---|
| 4,526,789 A | 7/1985 | Clark et al. |
| 4,620,979 A | 11/1986 | Schachar |
| 4,665,089 A | 5/1987 | Siezen et al. |
| 4,771,036 A | 9/1988 | Pigiet et al. |
| 4,808,182 A | 2/1989 | Barrett |
| 5,055,291 A | 10/1991 | Lam et al. |
| 5,091,421 A | 2/1992 | Clark et al. |
| 5,227,382 A | 7/1993 | Aziz et al. |
| 5,338,545 A | 8/1994 | Clark et al. |
| 5,375,611 A | 12/1994 | Lindqvist et al. |
| 5,614,587 A | 3/1997 | Rhee et al. |
| 5,658,592 A | 8/1997 | Tanihara et al. |
| 5,672,662 A | 9/1997 | Harris et al. |
| 5,756,672 A | 5/1998 | Builder et al. |
| 5,817,630 A | 10/1998 | Hofmann et al. |
| 6,027,745 A | 2/2000 | Nakada et al. |
| 6,103,756 A | 8/2000 | Gorsek |
| 6,291,466 B1 | 9/2001 | Gwon et al. |
| 6,294,518 B1 | 9/2001 | Potter et al. |
| 6,835,394 B1 | 12/2004 | Discher et al. |
| 6,945,971 B1 | 9/2005 | Gwon |
| 6,958,224 B2 | 10/2005 | Kumar et al. |
| 7,741,311 B2 | 6/2010 | Mousa et al. |
| 7,767,429 B2 | 8/2010 | Bookbinder et al. |
| 7,832,875 B2 | 11/2010 | Matic-Vujovic et al. |
| 8,758,802 B2 | 6/2014 | Muthukumar et al. |
| 9,061,050 B2 | 6/2015 | Gobin et al. |
| 9,675,589 B2 | 1/2017 | Muthukumar et al. |
| 9,789,091 B2 | 10/2017 | Muthukumar et al. |
| 2003/0130324 A1 | 7/2003 | McAvoy et al. |
| 2003/0223957 A1 | 12/2003 | Schwartz et al. |
| 2004/0038294 A1 | 2/2004 | Evangelista et al. |
| 2004/0043082 A1 | 3/2004 | Karageozian et al. |
| 2004/0120967 A1 | 6/2004 | Calvani |
| 2004/0254197 A1 | 12/2004 | Tasaka et al. |
| 2005/0079197 A1 | 4/2005 | Kataoka et al. |
| 2005/0249821 A1 | 11/2005 | Paul, Jr. |
| 2005/0260259 A1 | 11/2005 | Bolotin |

(Continued)

FOREIGN PATENT DOCUMENTS

| CA | 1269327 A | 5/1990 |
|---|---|---|
| CN | 1093259 A | 10/1994 |

(Continued)

OTHER PUBLICATIONS

International Search Report and Written Opinion; International Application No. PCT/US2016/061490; International Filing Date Nov. 11, 2016; dated Jan. 31, 2017; 18 pages.
Wang et al.; "Treatment with mPEG-SPA Improves the Survival of Corneal Grafts in Rats by Immune Camouflage"; Biomaterials; 43; pp. 13p-22p (2015).
"Secondary Cataracts: Cloudy Vision Cleared With Laser Treatment"; from Pacific Cataract and Laser Institute; www.pcli.com; copyright 2011; printed Apr. 28, 2017; 2 pages.
CN 1471924 A; published Feb. 4, 2004; Abstract only; 2 pages.
IN208748 A1, May 5, 2007, "Composition for Treatment of Cataract"; Rpendra et al.; English Abstract only; 1 page.
JP02-258727, published Oct. 19, 1990; Liposome Pharmaceutical Containing Gamma-L-Glutamyl-L-Cysteine Ester Derivative; from JP Office Action for Application P2012-543328; dated Aug. 26, 2014, Abstract only.

(Continued)

*Primary Examiner* — Jeffrey S Lundgren
*Assistant Examiner* — William Y Lee
(74) *Attorney, Agent, or Firm* — Cantor Colburn LLP (57) ABSTRACT

Described herein are methods of inhibiting or reversing the progression of cataract formation or presbyopia in an eye by administering a bifunctional molecule comprising a substituted or unsubstituted amine, succinimide, carboxylic acid, isocyanate, isothiocyanate, sulfonyl chloride, aldehyde, carbodiimide, acyl azide, anhydride, fluorobenzene, carbonate, N-hydroxysuccinimide ester, imidoester, epoxide or fluorophenyl ester covalently linked to a molecular bristle. Both presbyopia and cataracts are caused by aggregation of the soluble crystalline lens proteins called the crystallins.

5 Claims, 8 Drawing Sheets

(56) References Cited

U.S. PATENT DOCUMENTS

| | | |
|---|---|---|
| 2006/0018874 A1 | 1/2006 | Radhakrishnan et al. |
| 2006/0147415 A1 | 7/2006 | Mousa et al. |
| 2007/0275098 A1 | 11/2007 | Banks |
| 2008/0094573 A1 | 4/2008 | Vermette et al. |
| 2008/0227700 A1 | 9/2008 | Ghosh et al. |
| 2009/0247604 A1 | 10/2009 | Tang et al. |
| 2009/0324691 A1 | 12/2009 | Mahadevan et al. |
| 2010/0210531 A1 | 8/2010 | Johnson et al. |
| 2014/0274962 A1 | 9/2014 | Muthukumar et al. |
| 2014/0315800 A1 | 10/2014 | Ochiai et al. |
| 2015/0010634 A1 | 1/2015 | Knappe et al. |
| 2015/0157721 A1 | 6/2015 | Wu |
| 2015/0297740 A1 | 10/2015 | Rau et al. |
| 2016/0000707 A1 | 1/2016 | Muthukumar et al. |
| 2016/0074370 A1 | 3/2016 | Muthukumar et al. |
| 2017/0231905 A1 | 8/2017 | Muthukumar et al. |

FOREIGN PATENT DOCUMENTS

| | | |
|---|---|---|
| CN | 1621091 | 6/2005 |
| CN | 1660920 | 8/2005 |
| CN | 102172410 | 9/2011 |
| CN | 102579353 A | 7/2012 |
| DE | 3906311 A1 | 8/1990 |
| EP | 0641563 A1 | 3/1995 |
| EP | 1437143 A1 | 7/2004 |
| EP | 3373921 B1 | 8/2019 |
| IN | 208748 A1 | 5/2007 |
| JP | 2004161731 | 6/2004 |
| KR | 2010000203 | 1/2010 |
| WO | 199200748 A1 | 1/1992 |
| WO | 199300109 A1 | 1/1993 |
| WO | 9323032 A1 | 11/1993 |
| WO | 9416648 | 8/1994 |
| WO | 199416648 A1 | 8/1994 |
| WO | 9514482 A1 | 6/1995 |
| WO | 199514482 A1 | 6/1995 |
| WO | 199524899 A1 | 9/1995 |
| WO | 2000071723 A2 | 11/2000 |
| WO | 200191775 A3 | 12/2001 |
| WO | 200248190 A1 | 6/2002 |
| WO | 2003003073 A1 | 1/2003 |
| WO | 2005117987 A1 | 12/2005 |
| WO | 2006091796 A2 | 8/2006 |
| WO | 2007025763 A2 | 3/2007 |
| WO | 2008145721 A2 | 12/2008 |
| WO | 2009051223 A1 | 4/2009 |
| WO | 2010007626 A1 | 1/2010 |
| WO | 2010065024 A1 | 6/2010 |
| WO | 2010130638 A1 | 11/2010 |
| WO | 2011075430 A1 | 6/2011 |
| WO | 2012059882 A2 | 5/2012 |
| WO | 2012109975 A1 | 8/2012 |
| WO | 2012135682 A2 | 10/2012 |
| WO | 2012142659 A1 | 10/2012 |
| WO | 2012167081 A1 | 12/2012 |
| WO | 2014071132 A1 | 5/2014 |
| WO | 2014152818 A1 | 9/2014 |
| WO | 2014171842 A1 | 10/2014 |

OTHER PUBLICATIONS

PEGylation Reagents (linkers, crosslinkers and labels)_Products Description; by Uptima; uptima@interchim.com; printer Nov. 30, 2012; 12 pages.

PH Value Eye Drops, A Not Too Scientific Description of pH Value Eye Drops, Aug. 22, 2014.

Qian, et al.; "Effects of Anionic Surfactant SDS on the Photophysical Properties of Two Fluorescent Molecular Sensors"; Journal of Photochemistry and Photobiology; 200; pp. 402-409; (2008).

Wang et al.; "Safety and Efficacy of Intracapsular Tranilast Microspheres in Experimental Posterior Capsule Opacification"; Journal Cataract and Refractive Surgery; 33; pp. 2122-2128; (2007).

SG Search Report and Written Opinion; Application No. 11201507209S ; Application filing date Mar. 14, 2014; 13 pages; dated Feb. 7, 2017.

Liu et al.; "Separation of Polyethylene Glycols and Their Amino-Substituted Derivatives by High-Performance Gel Filtration Chromatography at Low Ionic Strength With Refractive Index Detection"; Journal of Chromatography A, 1046; pp. 121-126; (2004).

Margalit et al.; "Gioadhesives for Intraocular Use"; Retina 20, pp. 469-477; (2000).

METHODS OF INHIBITING CATARACTS AND PRESBYOPIA

CROSS-REFERENCE TO RELATED APPLICATIONS

This application claims priority to U.S. Provisional Application 62/254,863 filed on Nov. 13, 2015, which is incorporated herein by reference in its entirety.

FIELD OF THE DISCLOSURE

The present disclosure relates to compositions and methods of inhibiting or reversing the progression of age related changes in the crystalline lens of an eye.

BACKGROUND

The crystalline lens of the eye is a transparent structure that is suspended immediately behind the iris, which brings rays of light to a focus on the retina. The lens contains both soluble and insoluble proteins; together they constitute 35 percent of the wet weight of the lens. In a young, healthy lens, the soluble proteins, commonly referred to as crystallins, constitute 90 percent of the lens proteins. During the aging process, the lens crystallins form insoluble aggregates, which, at least in part, account for the decreased deformability of the lens nucleus, which characterizes presbyopia, the loss of the eye's ability to change focus to see near objects. The formation of insoluble aggregates of lens crystallins in presbyopia is believed to be an early stage in the formation of age-related cataracts.

Cataracts are defined by cloudiness or opacification in the crystalline lens of the eye. As an individual ages, cataracts form as the crystallins present in the lens are converted into aggregates, resulting in increased lens opacity. Specifically, there is a progressive decrease in the concentration of the soluble chaperone, α-crystallin, in human lens nuclei with age, as it becomes incorporated into high molecular weight aggregates and insoluble protein. The presence of aggregates compromises the health and function of the lens and left untreated, cataracts can lead to substantial vision loss or even blindness. Presently, the most common treatment for cataracts is surgery.

Crystallins are structural proteins most highly expressed in the lens fiber cells of the vertebrate eye. The crystallins are divided into two subfamilies: the α-crystallins (αA and αB) which are members of the small heat shock protein superfamily, also functioning as structural proteins and molecular chaperones; and the evolutionarily-linked superfamily of β- and γ-crystallins which function primarily as structural proteins in the lens, and contribute to the transparency and refractive properties of lens structure. In addition to their role in cataract development, αA-crystallin and αB-crystallin have been implicated in neurodegenerative diseases, like Alexander's disease, Creutzfeldt-Jacob disease, Alzheimer's disease and Parkinson's disease.

U.S. Patent Application 2008/0227700 describes deaggregation of proteins using peptides having chaperone activities as a therapeutic treatment. Specifically, αB peptides were used to deaggregate pH-induced aggregates of β-crystallin as measured by light scattering. Provision of a continuous supply of alpha crystallins into the lens is a challenge. What is needed are alternative methods suitable for the deaggregation of crystallins for the inhibition and/or reversal of cataracts and presbyopia.

SUMMARY

In an aspect, an ophthalmic composition comprises a bifunctional molecule, the bifunctional molecule comprising a substituted or unsubstituted amine, succinimide, carboxylic acid, isocyanate, isothiocyanate, sulfonyl chloride, aldehyde, carbodiimide, acyl azide, anhydride, fluorobenzene, carbonate, N-hydroxysuccinimide ester, imidoester, epoxide or fluorophenyl ester; covalently linked to a molecular bristle, wherein the molecular bristle is a polyethylene glycol having 1 to 3 oxyethylene groups; an alkoxy-polyethylene glycol having 1 to 3 alkoxyethylene groups, or an aryloxypolyethylene glycol having 1 to 3 aryloxyethylene groups.

In another aspect, a method of inhibiting or reversing the progression of cataract formation, presbyopia, or age related degeneration of a crystallin lens in an eye comprises contacting the eye with an effective cataract-inhibiting amount of an ophthalmic composition comprising a bifunctional molecule, the bifunctional molecule comprising a substituted or unsubstituted amine, succinimide, carboxylic acid, isocyanate, isothiocyanate, sulfonyl chloride, aldehyde, carbodiimide, acyl azide, anhydride, fluorobenzene, carbonate, N-hydroxysuccinimide ester, imidoester, epoxide or fluorophenyl ester; covalently linked to a molecular bristle, wherein the molecular bristle is a polyethylene glycol having 1 to 3 oxyethylene groups, an alkoxy-polyethylene glycol having 1 to 3 alkoxyethylene groups, or an aryloxypolyethylene glycol having 1 to 3 aryloxyethylene groups.

In another aspect, an ophthalmic composition further comprises at least a second bifunctional molecule comprising a substituted or unsubstituted amine, succinimide, carboxylic acid, isocyanate, isothiocyanate, sulfonyl chloride, aldehyde, carbodiimide, acyl azide, anhydride, fluorobenzene, carbonate, N-hydroxysuccinimide ester, imidoester, epoxide or fluorophenyl ester; covalently linked to a second molecular bristle, wherein the second molecular bristle is a linear or branched polyethylene glycol having 4 to 200 oxyethylene, alkoxyethylene or aryloxyethylene groups, poly(2-hydroxypropyl)methacrylamide (HPMA); poly(2-hydroxyethyl)methacrylate (HEMA); a ply(2-oxaziline), poly(m-phosphocholine), poly lysine, or poly glutamic acid, the second molecular bristle having a molecular weight of 150 to 8000.

The above-described and other features will be appreciated and understood by those skilled in the art from the following detailed description, drawings, and appended claims.

DETAILED DESCRIPTION

Disclosed herein are methods of disaggregating/preventing formation of a crystallin aggregate comprising contacting the crystallin aggregate with a composition comprising a bifunctional molecule in an amount sufficient to disaggregate and/or prevent formation of the crystallin aggregate. One of ordinary skill in the art would recognize that while the bifunctional molecules disclosed herein are generally described as a γ-crystallin charge masking agents, they are also expected to disaggregate/prevent protein aggregation of β-crystallin as well. Further disclosed are methods of inhibiting or reversing the progression of cataract formation in an eye which comprises contacting the eye with an effective cataract-inhibiting amount of an ophthalmic composition comprising the bifunctional molecules as described herein. Also disclosed are methods of inhibiting or reversing the progression of presbyopia in an eye which comprises contacting the eye with an effective presbyopia-inhibiting amount of an ophthalmic composition comprising the bifunctional molecules described herein.

The inventor has employed techniques such as dynamic light scattering to study the aggregates formed by γ-crystallins in solution. Both the β and γ-crystallins are highly stable structural proteins comprising four Greek-key motifs in two domains. While the β-crystallins form dimers as well as hetero- and homo-oligomers, the γ-crystallins are monomers in the eye. Further, while the β-crystallins exhibit a repulsive force in solution, the γ-crystallins exhibit an attractive interaction attributed to nonspecific protein or water interactions. It has also been hypothesized that thiol modifications cause aggregates of γ-crystallin to form in solution.

The human γ-crystallin family contains five members, the γA-D crystallins and γ-S crystallin. The γA-D crystallins are expressed early in development and are primarily found in the lens core; γC and γD-crystallin are most prevalent. Unfolding and refolding of γ-D crystallin in vitro has been shown to lead to increased protein aggregation due to the lack of stability of the refolded protein.

Without being held to theory, it is believed that the aggregation of γ-crystallin is both an electrostatic and a hydrophobic phenomenon, with the electrostatic forces dominating. Adding the heat shock proteins αA- and αB-crystallin disrupts γ-crystallin aggregation. A γ-crystallin charge masking agent that can disrupt electrostatic interactions can substitute for the chaperone activity of α-crystallin and prevent/reduce γ-crystallin aggregate size.

Administration of bifunctional molecules (e.g., γ-crystallin charge masking agents) can be used to treat diseases and/or conditions resulting from aggregation of γ-crystallins such as cataracts and presbyopia. As used herein, a cataract is an opacity of the crystalline lens of the eye caused by altered protein interactions in the lens. Protein interactions include misfolding of proteins as well as protein-protein interactions such as aggregation. Presbyopia is the impairment of vision due to advancing years or old age. Symptoms of presbyopia include decreased focusing ability for near objects, eyestrain, difficulty reading fine print, fatigue while reading or looking at an illuminated screen, difficulty seeing clearly up close, less contrast when reading print, need for brighter and more direct light for reading, needing to hold reading material further away in order to see it clearly, and headaches, especially headaches when using near vision. Individuals suffering from presbyopia may have normal vision, but the ability to focus on near objects is at least partially lost over time, and those individuals come to need glasses for tasks requiring near vision, such as reading. Presbyopia affects almost all individuals over the age of 40 to a greater or lesser degree.

In the method of inhibiting the progression of cataract formation in an eye, the eye may already contain one or more developing or fully developed cataracts before it is contacted with the bifunctional molecules. Accordingly, the method can be used to inhibit the formation of further cataracts in the eye, or to inhibit the formation of mature cataracts from the developing cataracts already present in the eye. Alternatively, the eye may be free of any developing or fully developed cataracts before it is contacted with the bifunctional molecules.

In the method of reversing the progression of cataract formation in an eye, at least partial to full reversal of cataracts in the eye is achieved by contacting the eye with a bifunctional molecule as disclosed herein.

Similarly, in the method of inhibiting the progression of presbyopia in an eye, the individual may already be experiencing one or more symptoms of presbyopia before the eye is contacted with the bifunctional molecule. Accordingly, the method can be used to reduce the progression of the symptom(s) experienced, or to inhibit the formation of additional symptoms of presbyopia. Alternatively, the eye may be free of any symptoms of presbyopia before it is contacted with the bifunctional molecule.

In the method of reversing the progression of presbyopia in an eye, at least partial to full reversal of the symptoms of presbyopia in the eye is achieved by contacting the eye with a bifunctional molecule as disclosed herein.

As used herein, a γ-crystallin charge masking agent is a molecule suitable to interfere with electrostatic protein-protein interactions, such as γ-crystallin electrostatic protein-protein interactions, which lead to γ-crystallin aggregation. In one embodiment, the masking agent is not a polypeptide. γ-crystallin charge masking agents prevent γ-crystallin aggregates from forming and/or reduce the size of pre-formed aggregates.

In a specific embodiment, the γ-crystallin charge masking agent is a bifunctional molecule containing a functional group covalently linked to a molecular bristle. The bifunctional molecule interacts with charges on the γ-crystallin molecules, such as positively charged lysine and arginine residues and negatively charged glutamate and aspartate residues. The molecular bristle is a hydrophilic, water-soluble species that provides distance between the γ-crystallin molecules, preventing aggregation. Without being held to theory, it is believed that the bifunctional molecule interacts with the protein and effectively puts the molecular bristle onto the protein, and the functional group may be expelled during the reaction. The molecular bristle, which can interact with the crystallins via covalent, hydrophobic, or ionic interactions, prevents aggregation of the γ-crystallin molecules. Without being held to theory, it is believed that the bifunctional molecules described herein may also act as β-crystallin interaction inhibitors.

Figure 1:
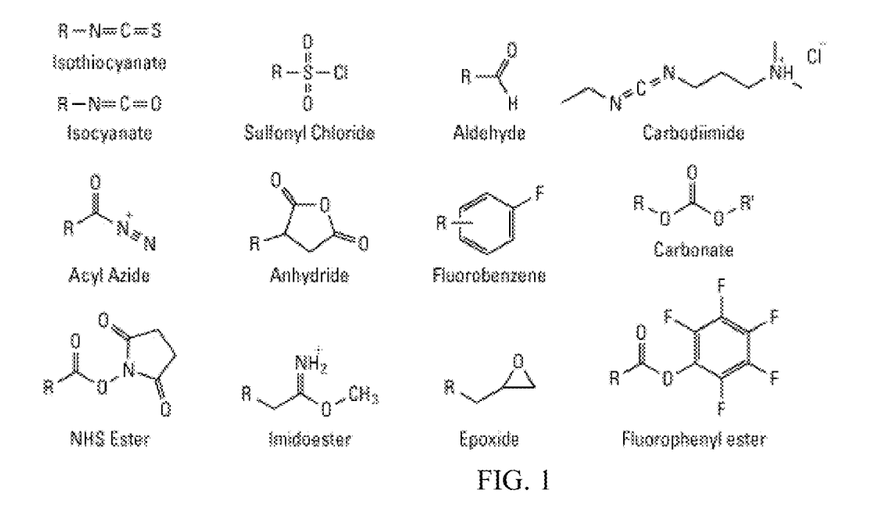
FIG. 1 shows embodiments of functional groups for the bifunctional molecules disclosed herein. In each structure, R is the molecular bristle.

Exemplary functional groups (which can be leaving groups or reactive groups, for example) include, by way of example, a substituted or unsubstituted amine, succinimide, carboxylic acid, isocyanate, isothiocyanate, sulfonyl chloride, aldehyde, carbodiimide, acyl azide, anhydride, fluorobenzene, carbonate, N-hydroxysuccinimide ester, imidoester, epoxide or fluorophenyl ester. FIG. 1 shows embodiments of functional groups wherein the R group is the molecular bristle. Without being held to theory, when the bifunctional molecule contains COOH, water leaves when it reacts with a protein's amine group. Without being held to theory, when the bifunctional molecule contains N-hydroxysuccinimide water is not released. In an NH$_2$ reaction, water leaves when NH$_2$ reacts with a COOH group on the protein.

Exemplary molecular bristles include linear or branched polyethylene glycols having one to three oxyethylene groups, modified polyethylene glycols such as alkoxy- and aryloxy polyethylene glycols having one to three oxyethylene, alkloxy ethylene or aryloxy ethylene groups. In a specific embodiment, the bifunctional γ-crystallin charge masking agent is:

NHS(PEG)$_n$

CA(PEG)n

In an embodiment, the ophthalmic composition further comprises at least a second bifunctional molecule, the at least second bifunctional molecule comprising a substituted or unsubstituted amine, succinimide, carboxylic acid, isocyanate, isothiocyanate, sulfonyl chloride, aldehyde, carbodiimide, acyl azide, anhydride, fluorobenzene, carbonate, N-hydroxysuccinimide ester, imidoester, epoxide or fluorophenyl ester, covalently linked to a second molecular bristle, wherein the second molecular bristle is a polyethylene glycol, an alkoxy-polyethylene glycol, or an alkoxypolyethylene glycol having 4 to 200 oxyethylene, alkoxyethylene or aryloxyethylene groups; poly(2-hydroxypropyl)methacrylamide (HPMA); poly(2-hydroxyethyl)methacrylate (HEMA); a ply(2-oxaziline), poly(m-phosphocholine), poly lysine, or poly glutamic acid, the second molecular bristle having a molecular weight of 150 to 8000.

The bifunctional molecule and the at least second bifunctional molecule can be present at any weight ratio, such as 1:99 to 99:1.

In one embodiment, the bifunctional molecules described herein are also useful in the treatment of diseases relating to protein folding such as Alzheimer's disease, Parkinson's disease, and Huntington's disease. In a specific embodiment, the bifunctional molecules are administered as oral compositions in the treatment of diseases relating to protein folding.

An advantage of the γ-crystallin charge masking agents described herein is that they are expected to be effective in the presence of post-translational modifications of γ-crystallins, including, for example, transamidation, oxidation, modified and dysfunctional connexins, and high concentrations of inorganic and organic ions such as $Ca^{+2}$.

The bifunctional molecules are contacted with the eye to inhibit the progression of cataracts and/or reduce existing cataracts, or to inhibit and/or reduce the symptoms of presbyopia. As used herein, the term "contacting the eye" encompasses methods of directly applying the bifunctional molecules to the eye. In the above-described method, suitable means known to those of ordinary skill in the art may be used to contact the eye with the bifunctional molecules. Examples of such methods include, but are not limited to, the compound being injected into the eye, being dropped or sprayed into the eye, applied in the form of an ophthalmic device, applied by iontophoresis, or otherwise topically applied to the eye.

As used herein, the term "effective cataract-inhibiting amount" means an amount which will inhibit the progression or formation of cataracts in an eye or inhibit the progression or formation of mature cataracts from developing cataracts already present in the eye. The effective cataract-inhibiting amount of the γ-crystallin charge masking agent will depend on various factors known to those of ordinary skill in the art. Such factors include, but are not limited to, the size of the eye, the number and progression of any fully developed or developing cataracts already present in the eye, and the mode of administration. The effective cataract-inhibiting amount will also depend on whether the pharmaceutical composition is to be administered a single time, or whether the pharmaceutical composition is to be administered periodically, over a period of time. The period of time may be any number of days, weeks, months, or years. In one embodiment, the effective cataract-inhibiting amount of the γ-crystallin charge masking agent, specifically the bifunctional molecules described herein, is about 0.001 g to about 0.1 g. More specifically, the effective cataract-inhibiting amount can be about 0.01 g to about 0.05 g. Exemplary amounts of the bifunctional molecules in the ophthalmic compositions are 0.00005 wt % to 50 wt %, or higher, for example, more specifically 0.01 wt % to 10 wt %, and most specifically 1 wt % to 3 wt %.

As used herein, the term "effective presbyopia-inhibiting amount" means an amount which will reduce a symptom of presbyopia in an eye or inhibit the progression of additional symptoms of presbyopia in the eye. The effective presbyopia-inhibiting amount of the γ-crystallin charge masking agent will depend on various factors known to those of ordinary skill in the art. Such factors include, but are not limited to, the size of the eye, the number and type of symptoms already present in the individual, and the mode of administration. The effective cataract-inhibiting amount will also depend on whether the pharmaceutical composition is to be administered a single time, or whether the pharmaceutical composition is to be administered periodically, over a period of time. The period of time may be any number of days, weeks, months, or years. In one embodiment, the effective presbyopia-inhibiting amount of the γ-crystallin charge masking agent, specifically the bifunctional molecules described herein, is about 0.001 g to about 0.1 g. Specifically, the effective presbyopia-inhibiting amount can be about 0.01 g to about 0.05 g. Exemplary amounts of the bifunctional molecules in the ophthalmic compositions are 0.00005 wt % to 50 wt %, or higher, for example, more specifically 0.01 wt % to 10 wt %, and most specifically 1 wt % to 3 wt %.

As used herein the term "ophthalmic composition" refers to a pharmaceutically acceptable formulation, delivery device, mechanism or system suitable for administration to the eye. The term "ophthalmic compositions" includes but are not limited to solutions, suspensions, gels, ointments, sprays, depot devices or any other type of formulation, device or mechanism suitable for short term or long term delivery of γ-crystallin charge masking agents, e.g., bifunctional molecules, to the eye. In contrast to oral formulations, for example, ophthalmic compositions exhibit specific technical characteristics associated with their application to the eyes, including the use of pharmaceutically acceptable ophthalmic vehicles that avoid inducing various reactions such as, for example, irritation of the conjunctiva and cornea, closure of the eyelids, secretion of tears and painful reactions. Specific ophthalmic compositions are advantageously in the form of ophthalmic solutions or suspensions (i.e., eye drops), ophthalmic ointments, or ophthalmic gels containing γ-crystallin charge masking agents, e.g., bifunctional molecules. Depending upon the particular form selected, the compositions may contain various additives such as buffering agents, isotonizing agents, solubilizers, preservatives, viscosity-increasing agents, chelating agents, antioxidizing agents, antibiotics, sugars, and pH regulators.

Examples of preservatives include, but are not limited to chlorobutanol, sodium dehydroacetate, benzalkonium chloride, pyridinium chlorides, phenethyl alcohols, parahydroxybenzoic acid esters, benzethonium chloride, hydrophilic dihalogenated copolymers of ethylene oxide and dimethyl ethylene-imine, mixtures thereof, and the like. The viscosity-increasing agents may be selected, for example, from methylcellulose, hydroxyethylcellulose, carboxymethylcellulose, hydroxypropylmethylcellulose, polyvinyl alcohol, carboxymethylcellulose, chondroitin sulfate, and salts thereof. Suitable solubilizers include, but are not limited to, polyoxyethylene hydrogenated castor oil, polyethylene glycol, polysorbate 80, and polyoxyethylene monostearate. Typical chelating agents include, but are not limited to, sodium edetate, citric acid, salts of diethylenetriamine pentaacetic acid, diethylenetriamine pentamethylenephosphonic acid, and stabilizing agents such as sodium edetate and sodium hydrogen sulfite.

Exemplary buffers include, but are not limited to borate buffers, phosphate buffers, carbonate buffers, acetate buffers and the like. The concentration of buffer in the ophthalmic compositions may vary from about 1 mM to about 150 mM or more, depending on the particular buffer chosen.

As used herein, the term "vehicle" is intended to include a carrier, diluent or excipient suitable for ophthalmic use. "Excipient" refers to an ingredient that provides one or more of bulk, imparts satisfactory processing characteristics, helps control the dissolution rate, and otherwise gives additional desirable characteristics to the compositions. In particular, the excipients are selected such that the ophthalmic composition does not trigger a secretion of tears that will entrain the active ingredient. Acceptable excipients are well known to a person skilled in the art, who will know how to select them depending on the desired formulation.

In one embodiment, the γ-crystallin charge masking agent is administered in the form of an ophthalmic device, such as a contact lens or a punctal plug. Suitable ophthalmic devices included biocompatible devices with a corrective, cosmetic or therapeutic quality.

In one embodiment, the γ-crystallin charge masking agent may be adhered to, incorporated into or associated with a contact lens, optionally as a controlled-release composition. The contact lens may be produced using known materials, for example, without limitation, hydrogels, silicone hydrogels, silicone elastomers and gas permeable materials such as polymethylmethacrylate (PMMA), methacrylic acid ester polymers, copolymers of oligosiloxanylalkyl(meth)acrylate monomers/methacrylic acid and the like. Specific examples of materials for water-containing soft ophthalmic lenses include those described in U.S. Pat. No. 5,817,726, 2-hydroxyethyl methacrylate polymers as described in U.S. Pat. No. 5,905,125, ophthalmic lens materials as described in European Patent Application No. 781,777, the hydrogel lens which is coated with a lipid layer in advance as described in U.S. Pat. No. 5,942,558; all incorporated herein for their teachings regarding contact lenses. Generally used contact lens such as hard or rigid cornea-type lens, and gel, hydrogel or soft-type lens which are produced from the above known materials may be used.

It is common in the contact lens industry to characterize contact lenses into two major categories; conventional and silicone hydrogels. The conventional based hydrogels started as poly(hydroxyethyl methacrylate) (poly HEMA) and evolved to polyHEMA copolymers with other hydrophilic moieties such as n-vinyl pyrrolidone (nVP), acrylamide, dimethyl acrylamide, and methacrylated phosphorylcholines. Polyvinyl alcohol lenses may also be employed.

The silicone hydrogels (SiH) typically consist of copolymers of methacrylated or meth(acrylamide) silicone monomers, prepolymers or macromers with typical conventional hydrogel monomers. Examples of silicone monomers include, without limitation, tri substituted, tetra substituted, alkyl terminated, methacrylated polydimethylsiloxane (PDMS), and block copolymers of silicone and hydrophilic monomers. ABA triblock copolymers are common where the A group is a hydrophilic block and the B group is the silicone monomer block. In addition to the methacrylates, other reactive groups include vinyl, acrylamide, or any other reactive group capable of chain reaction polymerization. Crosslinking and polymerization can also be achieved via step-growth and other polymerization methods using monomers with at least bi-functionality. An example for step growth polymerization is the reaction of a hydroxyl group with a carboxylic acid group in two amino acids or from terepthalic acid and ethylene glycol.

Plasma based coating methods are commonly used on silicone hydrogels including plasma oxidation and plasma coatings.

A sustained-release γ-crystallin charge masking agent composition may be produced, for example, by incorporating in, associating with or adhering to the contact lens the γ-crystallin charge masking agent composition according to the known methods for producing the contact lenses with sustained-release drugs as described in U.S. Pat. Nos. 5,658,592; 6,027,745; WO2003/003073; US-2005-0079197, incorporated herein for their teachings regarding contact lenses and sustained release, or by other suitable means. Specifically, without limitation, the contact lens may be produced by adhering the γ-crystallin charge masking agent to a part of a finely-divided or gel sustained-releasing agent such as polyvinyl pyrrolidone, sodium hyaluronate and the like. In addition, sustained release may be produced by forming a γ-crystallin charge masking agent composition reservoir such as by producing a contact lens from a member which forms a front surface of the lens and a member which forms a rear surface of the lens.

In one embodiment the charge masking agent may be inserted into the aqueous or vitreous as an injection with controlled release.

In one embodiment, the γ-crystallin charge masking agent is administered in a punctal plug. As used herein, the term punctal plug refers to a device of a size and shape suitable for insertion into the inferior or superior lacrimal canaliculus of the eye through, respectively, the inferior or superior lacrimal punctum.

In one embodiment, the γ-crystallin charge masking agent is administered by iontophoresis. Iontophoresis is a technique using a small electric charge to deliver a medicine or other chemical through the skin.

In one embodiment, the ophthalmic composition is administered using ultrasound enhancement.

The invention is further illustrated by the following non-limiting examples:

EXAMPLES

Methods

The γD- and γS-crystallin DNA sequences are in pQe1 plasmids that were provided by the King Labs at Massachusetts Institute of Technology (Cambridge, Mass.). γ-crystallin protein sequences contain a 6×N-terminal histidine tag (his tag) for purification purposes. The plasmids were transformed into a cloning competent cell line to create additional plasmid DNA. Plasmids were subsequently transformed into an expression competent cell line for protein synthesis (TAM 1 *E. coli* cells (Active Motif. Carlsbad, Calif.)).

γ-crystallin plasmid DNA was chemically transformed into M15pRep *E. coli* cells for protein synthesis. 1 L cultures were grown for protein purification. γ-crystallin protein was purified by Ni affinity chromatography. The N-terminal His tag contained on the γ-crystallin proteins preferentially binds to the Ni column. The bound protein can be eluted with an imidazole gradient which competitively binds to the Ni, releasing the purified protein. The procedure for purification is briefly (as before): protein is loaded on column, and washed first with 20 mM (0% B), then 35 mM (10% B), then 60 mM (20% B) imidazole. Protein is then eluted at 150 mM (57% B) imidazole. Purity was confirmed by SDS PAGE gel electrophoresis and fast protein liquid chromatography (FPLC).

Chemical Modification Protocol:
1) A batch of purified protein was buffer exchanged into PBS pH=6.8 using a HiTrap™ desalting column.
(2) Concentration ($A_{280}$) was measured prior to the addition of $CA(PEG)_n$.
(3) 100 mg of $CA(PEG)_n$ was added to a 3-5 ml batch of the above protein.
(4) The mixture was placed on a shaker at 4° C. at 250 RPM overnight.

Example 1: Dynamic Light Scattering of Unmodified γD-Crystallin Protein

Figure 2:
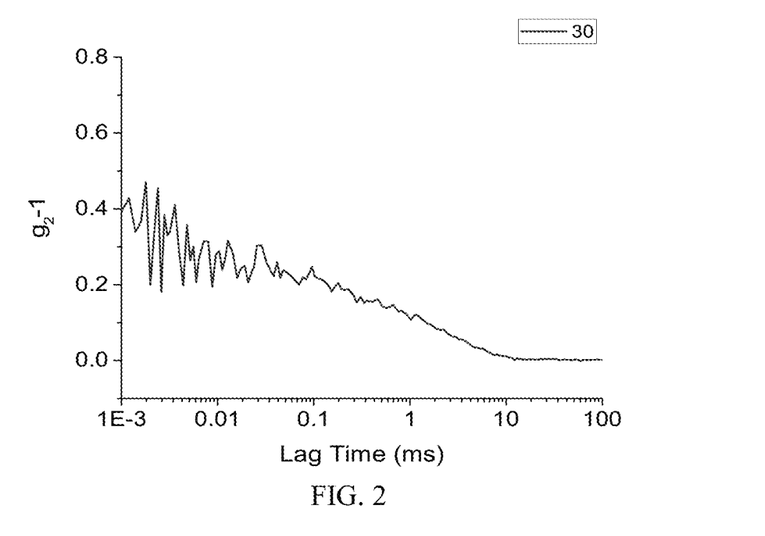
FIG. 2 shows the measured correlation function g2-1 plotted against the delay time (lag time) for the scattering angle of 30° for unmodified human γD-crystallin protein.
Figure 3:
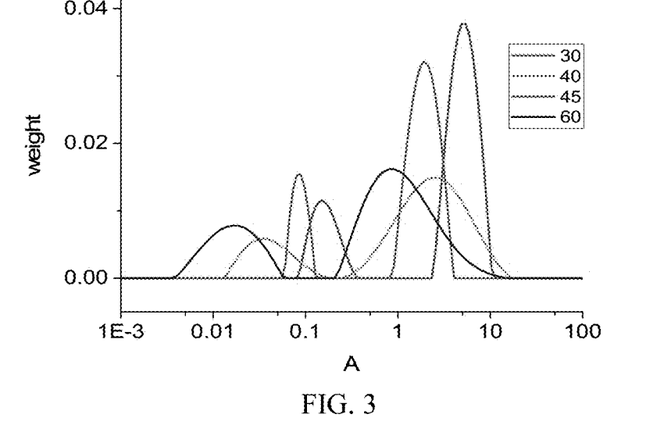
FIG. 3 shows the CONTIN analysis of the weight of various relaxation times for unmodified human γD-crystallin protein.
Figure 4:
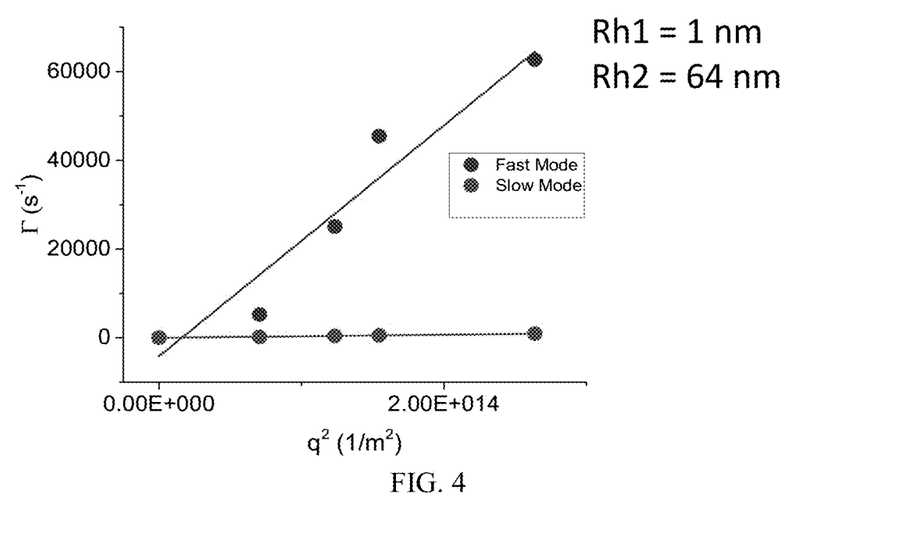
FIG. 4 shows the analysis of the data for human γD-crystallin protein using the theory of dynamic light scattering.

First a solution of unmodified γD-crystallin protein at a concentration of 0.1 mg/mL was studied by DLS. The measured correlation function g2-1 is plotted against the delay time (lag time) is given for the scattering angle of 30° in FIG. 2. The CONTIN analysis of the weight of various relaxation times is given in FIG. 3 for scattering angles ranging from 30° to 60°. It is clear that there are two populations in the solution, one corresponding to aggregates and the other corresponding to unaggregated protein. The analysis of these data using theory of dynamic light scattering, as given in FIG. 4, shows that the corresponding hydrodynamic radius of gyration are 64 nm, and 1.2 nm, respectively.

Figure 5:
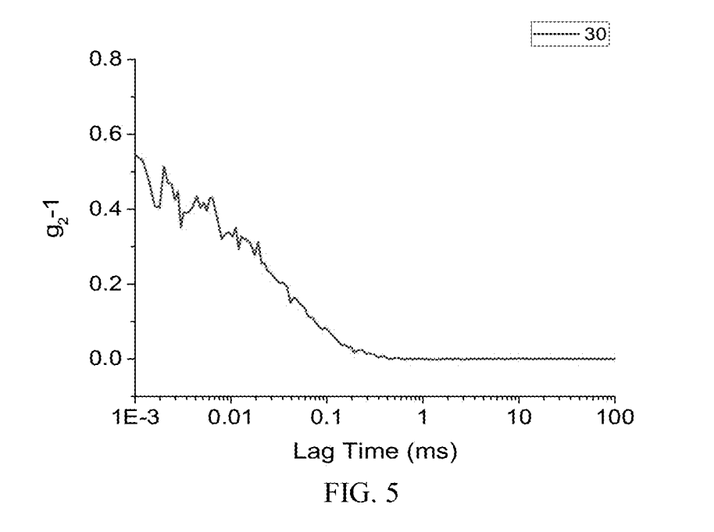
FIG. 5 shows the measured correlation function g2-1 plotted against the delay time (lag time) for the scattering angle of 30° for human γD-crystallin protein modified with CA(PEG)$_4$.
Figure 6:
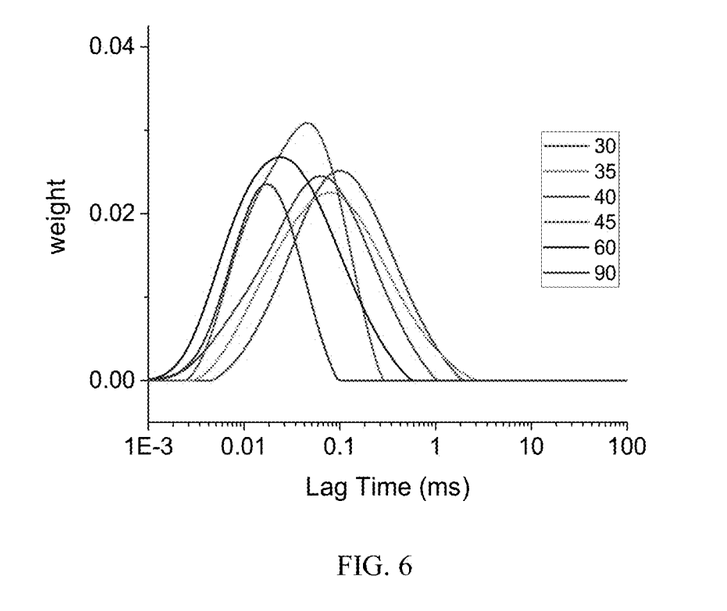
FIG. 6 shows the CONTIN analysis of the weight of various relaxation times for unmodified human γD-crystallin protein modified with CA(PEG)$_4$.
Figure 7:
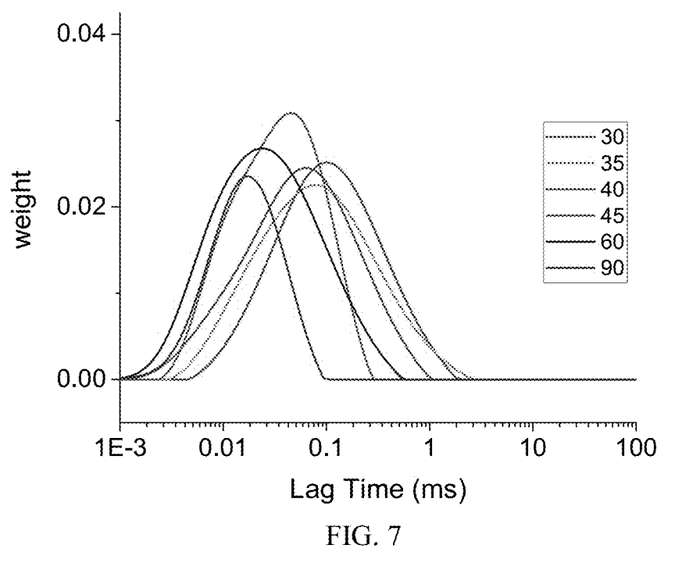
FIG. 7 shows the analysis of the data for γD-crystallin protein modified with CA(PEG)$_4$ using theory of dynamic light scattering.
Figure 8:
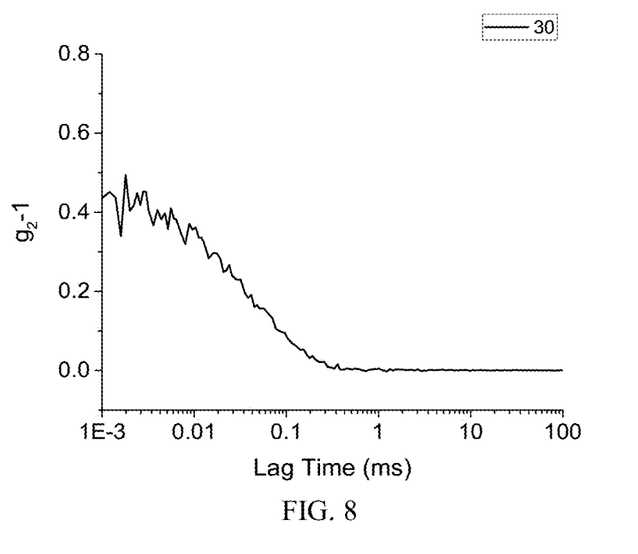
FIG. 8 shows the measured correlation function g2-1 plotted against the delay time (lag time) for the scattering angle of 30° for human γD-crystallin protein modified with CA(PEG)$_1$.
Figure 9:
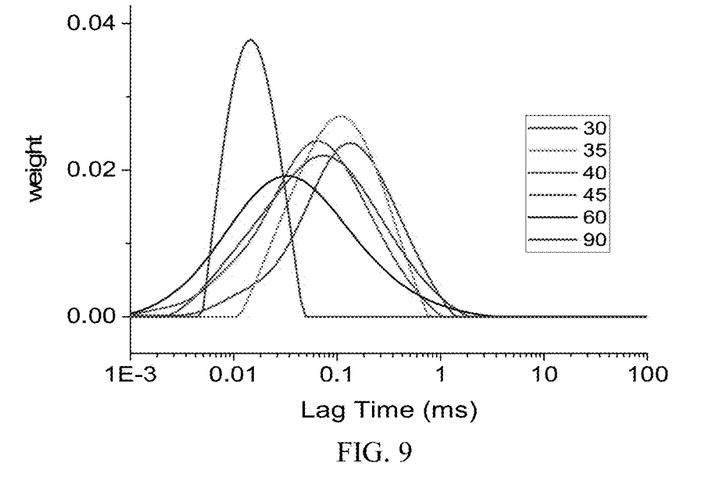
FIG. 9 shows the CONTIN analysis of the weight of various relaxation times for unmodified human γD-crystallin protein modified with CA(PEG)$_1$.
Figure 10:
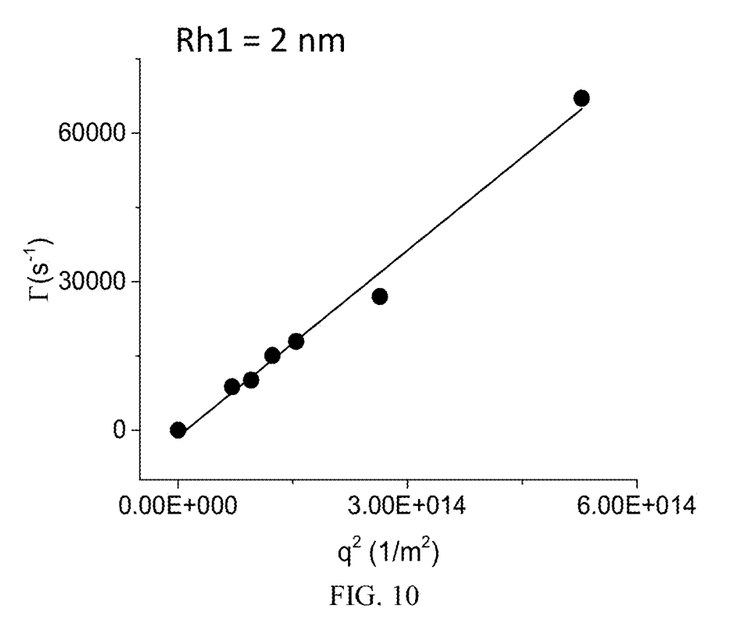
FIG. 10 shows the analysis of the data for human γD-crystallin protein modified with CA(PEG)$_1$ using the theory of dynamic light scattering.

Example 2: Dynamic Light Scattering of γD-Crystallin Protein Modified with $CA(PEG)_4$ The corresponding results as Example 1 for modifications by $CA(PEG)_4$ are given in FIGS. 5-7, with the result that the aggregate is absent and the size of the unaggregated protein is 2 nm. The concentration is 0.9 mg/mL of protein and 33 mg/ml of $CA(PEG)_4$. $CA(PEG)_4$ is Example 3: Dynamic Light Scattering of γD-Crystallin Protein Modified with $CA(PEG)_1$ The corresponding results as Example 1 for modifications by $CA(PEG)_1$ are given in FIGS. 8-10, with the result that the aggregate is absent and the size of the unaggregated protein is 2 nm. The concentration is 0.9 mg/mL of protein and 33 mg/ml of $CA(PEG)_1$. $CA(PEG)_1$ is

Figure 11:
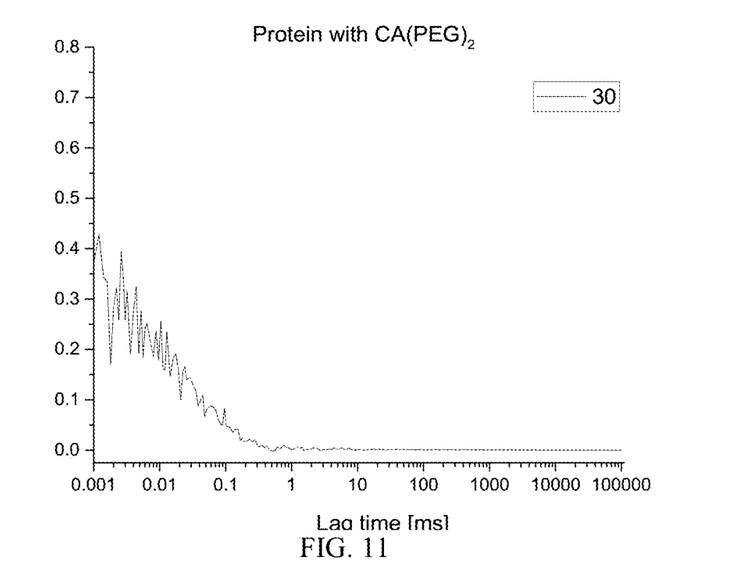
FIG. 11 shows the measured correlation function g2-1 plotted against the delay time (lag time) for the scattering angle of 30° for human γD-crystallin protein modified with CA(PEG)$_2$.
Figure 12:
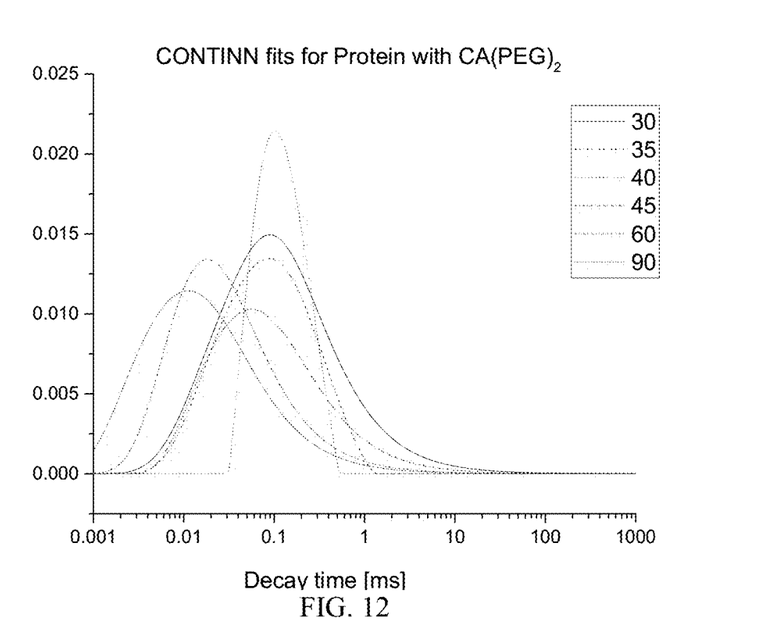
FIG. 12 shows the CONTIN analysis of the weight of various relaxation times for unmodified human γD-crystallin protein modified with CA(PEG)$_2$.
Figure 13:
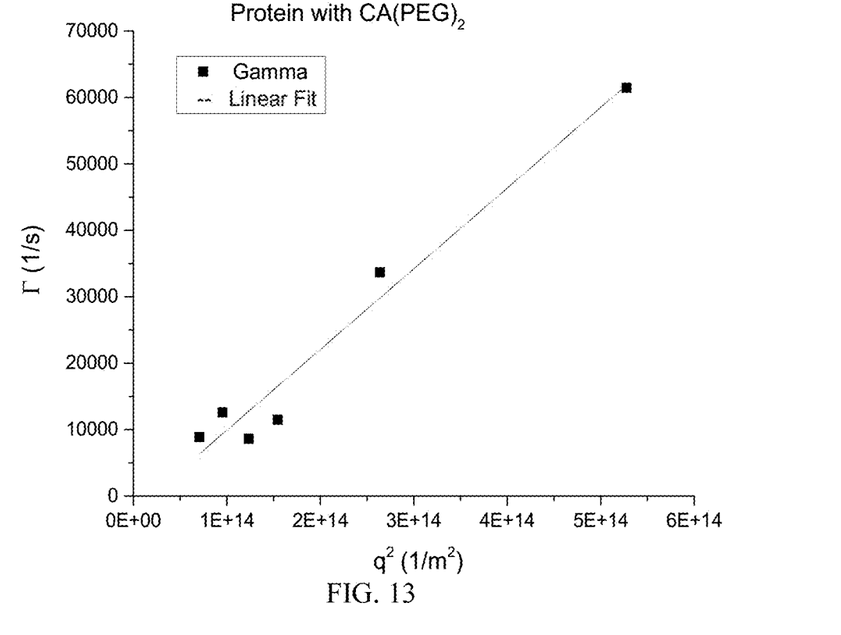
FIG. 13 shows the analysis of the data for human γD-crystallin protein modified with CA(PEG)$_2$ using the theory of dynamic light scattering.

Example 4: Dynamic Light Scattering of γD-Crystallin Protein Modified with $CA(PEG)_2$ The corresponding results as Example 1 for modifications by $CA(PEG)_2$ are given in FIGS. 11-13, with the result that the aggregate is absent and the size of the unaggregated protein is 2 nm. The concentration is 0.4 mg/mL of protein and 15 mg/ml of $CA(PEG)_2$. $CA(PEG)_2$ is

Figure 14:
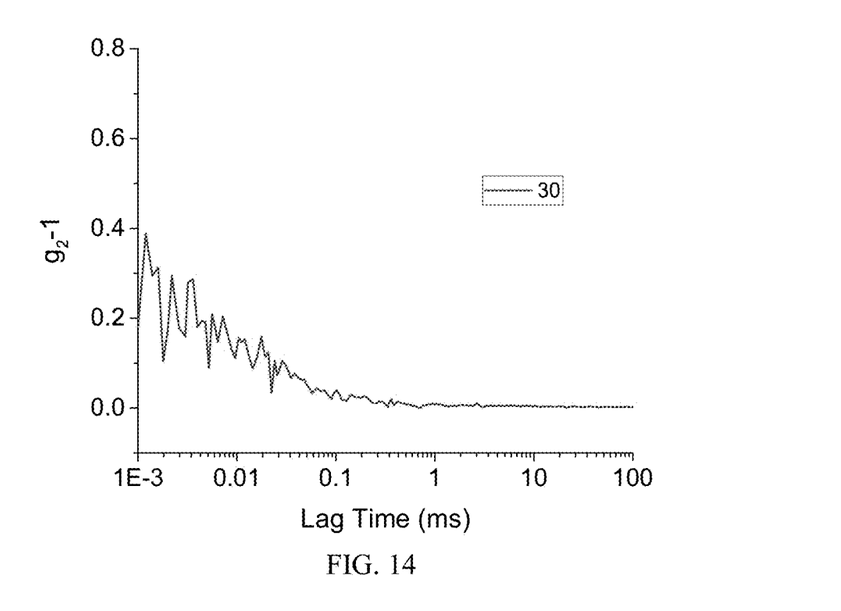
FIG. 14 shows the measured correlation function g2-1 plotted against the delay time (lag time) for the scattering angle of 30° for human γD-crystallin protein modified with CA(PEG)$_3$.
Figure 15:
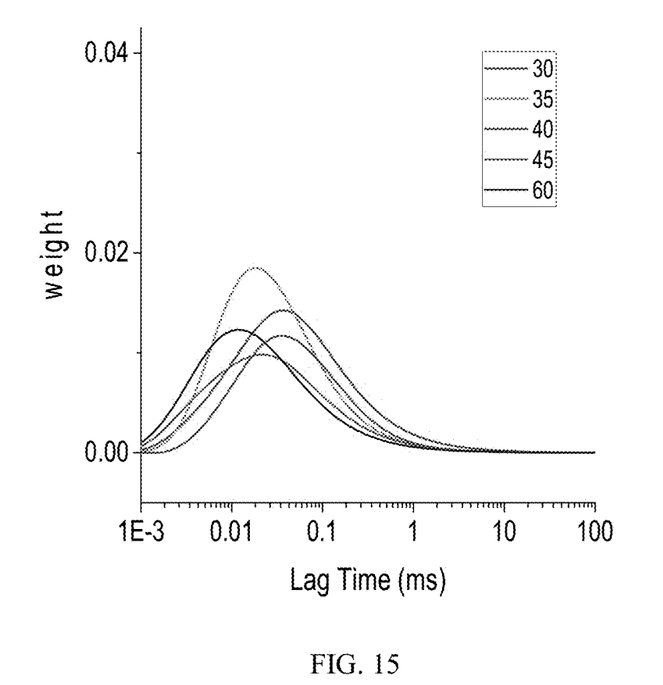
FIG. 15 shows the CONTIN analysis of the weight of various relaxation times for unmodified human γD-crystallin protein modified with CA(PEG)$_3$.
Figure 16:
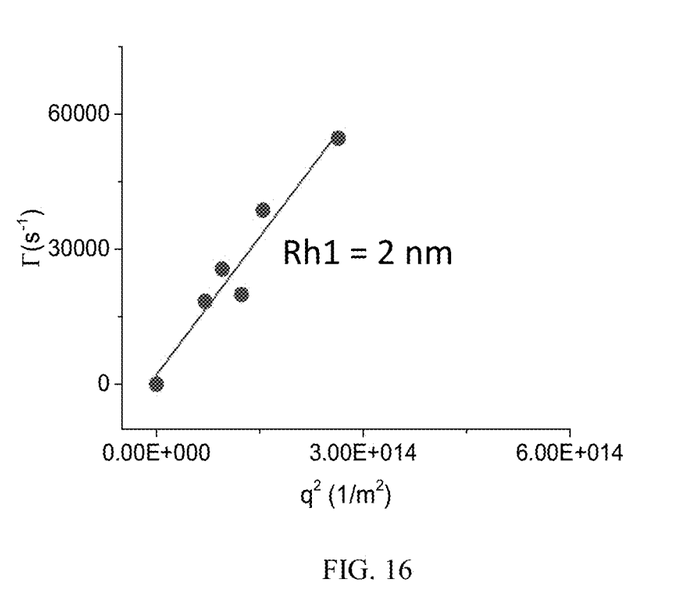
FIG. 16 shows the analysis of the data for human γD-crystallin protein modified with CA(PEG)$_3$ using the theory of dynamic light scattering.

Example 5: Dynamic Light Scattering of γD-Crystallin Protein Modified with CA(PEG)$_3$ The corresponding results as Example 1 for modifications by CA(PEG)$_3$ are given in FIGS. 14-16, with the result that the aggregate is absent and the size of the unaggregated protein is 2 nm. The concentration is 0.3 mg/mL of protein and 11 mg/ml of CA(PEG)$_3$. CA(PEG)$_3$ is Conclusion: All of CA(PEG)$_{14}$ are effective agents in completely preventing aggregation of γD-crystallin protein as determined by dynamic light scattering.

The term "substituted", as used herein, means that any one or more hydrogens on the designated atom or group is replaced with a substituent, provided that the designated atom's normal valence is not exceeded. Exemplary substituents include independently one or more alkyl groups, phenyl groups, cycloalkyl groups, halogens, halogenated alkyl groups and others, and/or combinations thereof.

As used herein, an "alkyl group", alone or as a part of a larger moiety (alkylamine, alkoxy and the like) is preferably a straight chain or branched saturated aliphatic group with 1 to about 12 carbon atoms, e.g., methyl, ethyl, n-propyl, iso-propyl, n-butyl, sec-butyl, tert-butyl, pentyl, hexyl, heptyl or octyl, or a saturated cycloaliphatic group with 3 to about 12 carbon atoms. Alkyl groups can optionally be independently substituted, such as with groups selected from C1-C12 alkyl, C6-C14 aryl, alkoxy, amine, esters such as —COO(R), acetates such as —O—CO—(R), ethers such as —C—O(R) and —O(C1-C12 alkyl), —COOH, halogens (preferably F, Cl, Br, or I), C1-C12 fluorinated or perfluorinated alkyl, —OH, —S(R), —SiO(R$_2$), —Si(R$_3$) and the like, where each R is independently an C1-C12 alkyl, C3-C10 cycloalkyl or C6-C14 aryl group.

The term "cycloalkyl", as used herein, means saturated cyclic hydrocarbons, i.e. compounds where all ring atoms are carbons. Examples of cycloalkyl include, but are not limited to, cyclopropyl, cyclobutyl, cyclopentyl, cyclohexyl, and cycloheptyl.

As used herein, an "aryl", alone or as part of a larger moiety (e.g. diarylamine) is a carbocyclic aromatic group, preferably including 6-22 carbon atoms. Examples include, but are not limited to, carbocyclic groups such as phenyl, naphthyl, biphenyl, and phenanthryl, and can optionally be independently substituted, such as with groups selected from C1-C12 alkyl, C6-C14 aryl, alkoxy, amine, esters such as —COO(R), acetates such as —O—CO—(R), ethers such as —C—O(R) and —O(C1-C12 alkyl), —COOH, halogens (preferably F, Cl, Br, or I), C1-C12 fluorinated or perfluorinated alkyl, —OH, —S(R) and —Si(R$_3$) and the like, where each R is independently an C1-C12 alkyl, C3-C10 cycloalkyl or C6-C14 aryl group.

The terms "alkoxy", as used herein, means an "alkyl-O—" group, wherein alkyl is defined above. Examples of alkoxy group include methoxy or ethoxy groups.

As used herein, the term amine includes NH$_2$ as well as alkylamines, arylalkylamines and arylamines, that is secondary or tertiary alkyl, aryl or arylalkyl amino groups, wherein the alkyl groups and aryl groups are as defined above. The point of attachment of the alkylamine, arylamine or arylalkylamine is on the nitrogen. Examples include methylamine, ethylamine, propylamine, isopropylamine, dimethylamine, diethylamine, dipropylamine, ethylpropylamine, ethylhexylamine, cyclohexylamine, phenethylamine, phenylisopropylamine and the like. The alkylamines, arylalkylamines and arylamines are not limited, and can be, for example, C$_1$-C$_{20}$ alkylamines, C$_6$-C$_{22}$ arylalkylamines, C$_6$-C$_{22}$ arylamines.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). All ranges disclosed herein are inclusive and combinable.

Embodiments are described herein, including the best modes known to the inventors. Variations of such embodiments will become apparent to those of ordinary skill in the art upon reading the foregoing description. The skilled artisan is expected to employ such variations as appropriate, and the disclosed methods are expected to be practiced otherwise than as specifically described herein. Accordingly, all modifications and equivalents of the subject matter recited in the claims appended hereto are included to the extent permitted by applicable law. Moreover, any combination of the above-described elements in all possible variations thereof is encompassed unless otherwise indicated herein or otherwise clearly contradicted by context.

The invention claimed is:

1. An ophthalmic composition comprising a bifunctional molecule, the bifunctional molecule comprising wherein the ophthalmic composition is an eye drop, an ophthalmic solution, an ophthalmic suspension, an ophthalmic ointment, a spray, or an ophthalmic gel.

2. The ophthalmic composition of claim 1, wherein the ophthalmic composition includes a buffering agent, an isotonizing agent, a solubilizer, a preservative, a viscosity-increasing agent, a chelating agent, an antioxidizing agent, an antibiotic, a sugar, a pH regulator, or a combination thereof.

3. The ophthalmic composition of claim 1, wherein the ophthalmic composition is an ophthalmic device.

4. The ophthalmic composition of claim 3, wherein the ophthalmic device is in the form of a contact lens or a punctal plug.

5. The ophthalmic composition of claim 1, wherein the ophthalmic composition is a sustained release composition.

* * * * *